United States Patent [19]

Kamphuis et al.

[11] Patent Number: 5,072,041
[45] Date of Patent: Dec. 10, 1991

[54] OPTICALLY ACTIVE N-HYDROXY-ALPHA-AMINO ACIDS, AMIDES AND THEIR DERIVATIVES

[75] Inventors: Johan Kamphuis; Wilhelmus H. J. Boesten, both of Sittard, Netherlands

[73] Assignee: Stamicarbon B.V., Geleen, Netherlands

[21] Appl. No.: 429,976

[22] Filed: Nov. 1, 1989

Related U.S. Application Data

[62] Division of Ser. No. 305,903, Feb. 3, 1989.

[30] Foreign Application Priority Data

Feb. 4, 1988 [NL] Netherlands .................. 8800260

[51] Int. Cl.$^5$ .................. C07C 229/08; C07C 229/36; C07C 237/06; C07C 237/20
[52] U.S. Cl. ................................. 564/164; 564/160; 564/198; 562/556; 562/557; 562/561; 562/567; 562/568; 562/575; 548/344; 548/496
[58] Field of Search ............... 564/164, 300, 160, 169, 564/198; 562/443, 575; 548/344, 496

[56] References Cited

U.S. PATENT DOCUMENTS

| | | | |
|---|---|---|---|
| 3,064,007 | 11/1962 | Krimm et al. | 548/959 |
| 4,172,846 | 10/1979 | Boesten | 562/444 X |
| 4,847,412 | 7/1989 | Boesten et al. | 548/344 X |

OTHER PUBLICATIONS

Grundke et al., Synthesis, (12), 1115-1116 (1987).
March, "Advanced Organic Chemistry", 2nd ed., McGraw-Hill, New York, 1977, p. 1107.
Polonski et al., I, Tetrahedron Letters, (28), 2453-56, (1974).
Polonski et al., II, Chemical Abstracts, vol. 93, No. 26754u (1980).
Polonski et al., III, Chemical Abstracts, vol. 90, No. 87876v (1979).
Chemical & Pharmaceutical Bulletin, vol. 28, No. 9, Sep. 1980, pp. 2720-2733, Pharmaceutical Society of Japan, Tokyo, JP; M. Mano et al.: "Anticoccidials. IV. A Convenient Synthesis of 2(1H)-Pyrazinone 4-oxide Derivatives".
Tetrahedron Letters, No. 28, Jul. 1974, pp. 2453-2456, Pergamon Press, Oxford, GB; T. Polonski et al.: "Oxidation of Amino Acid Esters into N-Hydroxy-Alpha-Amino Acids in Organic Chemistry".
Chemica Reviews, vol. 86, No. 4, Aug. 1986, pp. 697-700, American Chemical Society, U.S.; H. C. J. Ottenheijm et al.: "N-Hydroxy-Alpha-Amino Acids in Organic Chemistry".
E. Muller: "Methoden der Organischen Chemie", 4th edition, vol. X/4, 1968, pp. 409-410, (Houben-Weyl), Stuttgart, DE; W. Rundel: "Nitrone".
Pritzkow et al., Justus Liebigs Ann. Chem. 703, 66-76 (1967).
Willems et al., Chemical Abstracts, vol. 51, No. 17543e (1957).
Kaminski et al., Chemical Abstracts, vol. 79, No. 42819k (1973).

*Primary Examiner*—Mary C. Lee
*Assistant Examiner*—Fiona T. Powers
*Attorney, Agent, or Firm*—Cushman, Darby & Cushman

[57] ABSTRACT

The invention relates to new pure D- or L-N-hydroxy-alpha-amino acids and the derivatives thereof, including optically active N-hydroxy-phenylglycine amide, which has antibiotic and antitumor activity.

4 Claims, No Drawings

OPTICALLY ACTIVE N-HYDROXY-ALPHA-AMINO ACIDS, AMIDES AND THEIR DERIVATIVES

This is a division of application Ser. No. 07/305,903, filed Feb. 3, 1989.

The invention relates to a process for the preparation of N-hydroxy-alpha-amino acids and derivatives thereof by reacting an alpha-amino acid derivative with an aromatic aldehyde to form a Schiff base, oxidizing the Schiff base to an oxaziridine and converting the oxaziridine into the corresponding N-hydroxy-alpha-amino acid derivative and, if so desired, converting that derivative into the corresponding acid or into a different derivative.

There is an increasing interest in N-hydroxy-alpha-amino acids and derivatives thereof, such as esters, amides, etc., and also peptides which contain such compounds as building blocks. Such peptides cannot be prepared by oxidation of an N-H bond in a peptide consisting of one or more alpha-amino acids. The peptides referred to can only be prepared by coupling an N-hydroxy-alpha-amino acid derivative to one or more alpha-amino acids.

N-hydroxy-alpha-amino acids and/or derivatives thereof and also peptides thereof usually have biological activity and mostly antibiotic and/or antitumour activity. E. Buehler and G. B. Brown, J. Org. Chem. 32 (1967) 265, state that several N-hydroxyamino acids are components of several antibiotics that are obtained in microbiological fermentations and these authors mention a number of N-hydroxy-alpha-amino acids that are obtained from naturally occurring peptides.

A large number of synthesis reactions are known for N-hydroxy-alpha-amino acids and derivatives thereof. A survey is given in the article "N-hydroxy-alpha-amino acids in organic chemistry" by Harry C. J. Ottenheym and Jacobus D. M. Herscheid in Chem. Rev. 86 (1986) 697-707. This shows that there is a great interest in this type of compounds. In a previous article, in Synthesis 1980 890, M. W. Tijhuis, J. D. M. Herscheid and H. C.. Ottenheym pointed out that the synthesis reactions described so far were time-consuming, gave small yields and were of limited use.

The alpha-carbon atom of alpha-amino acids and derived compounds is almost always an asymmetrical carbon atom. The only case in which this carbon atom is not assymmetrical is if two equal atoms or radicals are bound to it, as is the case in, for example, glycine (amino-acetic acid). In all other cases there are stereoisomers of alpha-amino acids, N-hydroxy-alpha-amino acids and the derivatives thereof.

The aforementioned articles do not or hardly discuss the preparation of pure or virtually pure stereoisomers of the aforementioned compounds, although this is of great importance, particularly if the compounds are to be used for biological purposes, for example as antibiotics or as agents for inhibiting the growth of tumours. The great importance of this was not realized until in the past decennium. Receptors appear to play a role here.

Among the many synthesis reactions that have been suggested for N-hydroxy-alpha-amino acids or the derivatives thereof there is one that consists of the conversion of an ester of an amino acid with an aromatic aldehyde to a Schiff base, oxidation of the Schiff base to an oxaziridine and conversion of the oxaziridine into an N-hydroxy-alpha-amino acid or an ester thereof. This synthesis reaction is known from the article "Oxidation of amino acid esters into N-hydroxyamino acid derivatives" by T. Polonski and A. Chimiak; Tetrahedron Letters 1974, 2453-2456. However, this gives no or only an incomplete description of the way in which the different reactions are carried out. Apparently, no attention has been paid to this since this article, which is now 14 years old, in spite of the apparent interest in N-hydroxyamino acids. According to the aforementioned article, the conversion of an ester of an amino acid with an aromatic aldehyde is effected using the hydrochloride of that ester. For the conversion with an aromatic aldehyde to a Schiff base, the $NH_2 \cdot HCl$ group is converted in situ into the $NH_2$ group and according to the reaction equation this is done with triethylamine. Other data on the reaction conditions are lacking. Then the Schiff base is oxidized with peracetic acid to form an oxaziridine.

The first, virtually simultaneous descriptions of oxaziridines were by W. D. Emmons in J. Am. Chem. Soc. 78 (1956), 6208 and 79 (1957), 5739 and by L. Horner and E. Jurgens in Chem. Ber. 90 (1957), 2184, in which articles they are referred to as oxaziranes.

Oxaziridines are highly reactive compounds and Polonski and Chimiak (Loc. cit.) state that the conversion of esters of amino acids with anisaldehyde and oxidation of the resulting Schiff bases results in oxaziridines, which are highly sensitive to acids. When heated with hydrochloric acid, the oxaziridines produce N-hydroxyamino acids. When the hydrochlorides of amino acid esters are used, the yields obtained are always less than 50% and in many cases they are about 30%. In order to obtain esters instead of the corresponding acids, the oxaziridine ring must be opened under very mild conditions.

Another disadvantage of this process established by the applicant is that the conversion of an amino acid ester with an aromatic aldehyde must be carried out in complete absence of water, because otherwise the ester will be at least partly hydrolyzed to the corresponding acid. The acid does not react or hardly reacts with the aromatic aldehyde to form a Schiff base. Therefore, the conversion must be effected in an organic solvent that is free from water. Since water is produced in the reaction of an amino acid ester and an aromatic aldehyde, this water must be continuously removed from the reaction mixture, for example by distillation.

It has already been explained above that, in the case of biologically active compounds with possible stereoisomers, it must be possible to prepare the stereoisomer with the desired biological activity as free as possible from the other possible stereoisomer(s). In some cases it was found that one or more other stereoisomers may be very harmful and may lead to extremely undesired side effects. At best, other stereoisomers are not harmful, in which case they constitute undesired ballast in a biologically active compound. It is therefore desirable to be able to obtain N-hydroxy-alpha-amino acids and/or derivatives thereof as pure or virtually pure stereoisomers. Pure stereoisomers of alpha-amino acid esters are difficult to obtain, unless use is made of a pure stereoisomer of an alpha-amino acid.

It has now been found that N-hydroxy-alpha-amino acids can be prepared easily and with good yields by reacting an alpha-amino acid amide with an aromatic aldehyde, such as benzaldehyde, preferably a para-substituted benzaldehyde, such as anisaldehyde, to the corresponding Schiff base, oxidizing this Schiff base to the corresponding oxaziridine and converting the oxaziridine into N-hydroxy-alpha-amino acid amide. If so desired, the N-hydroxy-alpha-amino acid amide thus obtained can be converted into the corresponding acid or a different derivative thereof, including peptides, such as mono-N-hydroxydipeptides.

More specifically, the present invention relates to compounds with the general formula

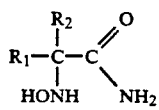

and the corresponding acids, esters and other derivatives, as well as to the preparation thereof using compounds with the general formula

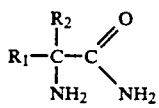

in which formulas $R_1$ represents H, acyclic or cyclic alkyl, whether or not substituted, or aryl, whether or not substituted, and $R_2$ represents H, acyclic or cyclic alkyl, whether or not substituted, or aryl, whether or not substituted, it being understood that substituents in the groups represented by $R_1$ and/or $R_2$ are not oxidized under the process conditions or can be protected from reacting under the process conditions by the introduction of protective groups.

If, for example, the alkyl or aryl groups represented by $R_1$ and/or $R_2$ are substituted by one or more thiol groups or primary or secondary amino groups, these groups must be protected. The way in which reactive groups can be protected is well known in the art and is not dealt with any further here.

Preferably, $R_2$ represents a hydrogen atom. More preferably, the present invention relates to N-hydroxy-alpha-amino acid amides and the corresponding acids, esters and other derivates that are derived from the known naturally occurring amino acids, in particular: glycine, alanine, valine, leucine, isoleucine, methionine, phenylalanine, tryptophan, serine, threonine, cysteine, tyrosine, asparagine, glutamine, aspartic acid, glutamic acid, lysine, arginine and histidine. Of these only glycine has a symmetrical alpha-carbon atom. The invention comprises both the L-form and the D-form and mixtures of the L- and D-forms of the N-hydroxy-alpha-amino acids and derivatives thereof that are derived from the other naturally occurring alpha-amino acids. Of course, this also applies to N-hydroxy-alpha amino acids and derivatives thereof that are not derived from the aforementioned naturally occurring amino acids.

The N-hydroxy-alpha-amino acids discussed here are new compounds. Pritzkow and Rösler, Liebigs Ann. Chem. 703 (1967) 66–67 have described alpha-hydroxylamine-isobutyric acid amide, alpha-hydroxyl-amine cyclohexane carboxylic acid amide and 4-methyl-1-hydroxylamine cyclohexane carboxylic acid amide. The applicant has found that the preparation method described by Pritzkow and Rösler is of very limited use only.

The first step of the process discussed here, the conversion of an alpha-amino acid amide with an aromatic aldehyde to form a Schiff base, can be effected in an aqueous medium and results in virtually quantitative yields. In this respect the present process differs extremely favourably from the aforementioned process according to Polonski and Chimiak (loc. cit.). The use of an alpha-amino acid amide as reaction component also presents the advantage that alpha-amino acid amides can easily be obtained in the form of pure stereoisomers. Mixtures of stereoisomers of an amino acid amide can be separated by hydrolyzing one of the isomers with an aminopeptidase, after which the remaining amide isomer can be separated from the acid formed. By then reconverting the hydrolyzed isomer into the amide again, both stereoisomers of the amide can be obtained in a pure form. Such a process is described in, for example, U.S. Pat. No. 3,971,700 and NL-A-75.13551. In this way, it is much easier to prepare pure stereoisomers of alpha-amino acid amides than to prepare pure stereoisomers of alpha-amino acid esters, in which case use must be made of the pure steroisomers of the acids.

Many processes are known for the preparation of individual stereoisomers of alpha-amino acids, for example conversion of a mixture of stereoisomer of such an acid with a stereoisomer of a base, selective crystallization of the salt thus formed and conversion of a stereoisomer of the salt into the acid. If the acid must be esterified, losses will occur in the process and there will mostly also be a certain degree of racemization. Because of this, the preparation of stereoisomers of alpha-amino acid esters is a much more time-consuming process than the preparation of stereoisomers of alpha-amino acid amides and, moreover, the yield of esters in the overall conversion reaction is much lower than that of amides. Alpha-amino acid amides can be prepared with very good yields from alpha-amino nitriles and in the manner mentioned above the alpha-amino acid amides can then easily, and with high yields, be separated into the individual stereoisomers. The conversion of a stereoisomer of an alpha-amino acid amide into the corresponding N-hydroxy-alpha-amino acid amide according to the present invention does not only appear to result in very high yields, as already mentioned above, but it also takes place without any racemization.

This the applicant discovered by converting a stereoisomer of an alpha-amino acid amide into an N-hydroxy-alpha-amino-acid amide according to the present process and then reducing the latter back to an alpha-amino acid amide with hydrogen and the aid of a Pd/C catalyst. The possible stereoisomers of the alpha-amino acid amides and N-hydroxy-alpha-amino acid amides investigated are enantiomers. The optical activity is a measure of the purity.

The alpha-amino acid amide obtained in the reduction reaction appeared to present the same specific rotation as the alpha-amino acid amide used as starting material. From this it can be concluded that no racemization whatsoever took place. This is a great advantage, because it is known that racemization occurs in very many conversions, even in conversions that do not involve the asymmetric carbon atom itself.

The Schiff base that is formed in the reaction of an alpha-amino-acid amide and an aromatic aldehyde is very insoluble in water. If this conversion is effected in an aqueous medium, the Schiff base precipitates and can easily be recovered by filtration. As already mentioned above, the Schiff base yields are practically quantitative.

The Schiff base is then oxidized into an oxaziridine. The oxidation of the Schiff base must be effected in such a manner that it does not proceed any further once oxaziridine is obtained. Any person skilled in the art can easily determine how to effect the oxidation while ensuring that it does not proceed beyond the oxaziridines. Organic peracids, such as peracetic acid, perbenzoic acid, chloroperbenzoic acid, monoperphthalic acid, etc., appeared to be particularly suitable for this purpose. Highly suitable is m-chloroperbenzoic acid. This oxidation can be carried out in a suitable manner by dissolving the Schiff base in an organic solvent that is free from water, such as dichloromethane, an ether, which may also by cyclic such as dioxane, tetrahydrofuran, etc.

Using m-chloroperbenzoic acid presents an advantage, because it dissolves in a solvent like dichloromethane, in which the Schiff base is also soluble. The oxidation, which is preferably effected at room temperature, results in oxaziridine that is soluble in the organic solvent, and m-chlorobenzoic acid, which is insoluble in, for example, dichloromethane and therefore precipitates, after which it can be removed by filtration.

Without being isolated from the solution, the oxaziridine can then be converted into the corresponding N-hydroxy-alpha-amino acid amide by acid hydrolysis. This hydrolysis must be carried out carefully to avoid hydrolysis of the amide group. The reason for this is that the hydroxyamino acid that is formed in further hydrolysis is not very stable and partial decaboxylation takes place in an acid medium, which may cause considerable losses. The acid hydrolysis must be carried out in a moderately acid medium. The hydrolysis may, for example, be effected in a suitable manner with hydroxylamine hydrochloride ($NH_2OH \cdot HCl$), a weakly acidically reacting compound, the pH of a 0.1 m solution of which amounts to 3.4 at 25° C. Other acid compounds with a similar acidity may also be used.

The hydroxylamine hydrochloride that is preferably to be used is not very soluble in apolar solvents such as dichloromethane, but is very soluble in alcohols, in particular in methanol (at 25° C., 17.5 g/100 g) and therefore the hydrolysis is preferably effected in an alcoholic, more preferably a methanolic medium. The oxaziridine solution in dichloromethane can be evaporated and the residue introduced into, for example, methanol, but it is also possible to add, for example, methanol to the solution in dichloromethane. The hydrolysis proceeds faster in an alcoholic medium than in an alcohol-dichloromethane mixture and therefore evaporation and introduction into an alcohol are preferable.

The solution of the oxaziridine in an alcohol or a mixture of an alcohol and a non-polar or slightly polar solvent, such as dichloromethane, to which, for example, hydroxylamine hydrochloride has been added, is stirred at ambient temperature until the oxaziridine has been hydrolyzed, which usually takes a few hours. Then an apolar solvent, such as ether, is added to precipitate the N-hydroxy-alpha-amino acid amide as HCl salt, which can then be recovered by separation, for example by filtration.

The embodiments described above of the preparation of N-hydroxy-alpha-amino acid amides were only described for a better understanding of the invention. It will, however, be clear that the invention is not limited thereto and that the invention comprises any embodiment according to which the steps of the process according to the invention, being: (1) conversion of alpha-amino acid amide and aromatic aldehyde into a Schiff base, (2) oxidation of the Schiff base into oxaziridine, (3) conversion of oxaziridine into N-hydroxy-alpha-amino acid amide, can be carried out.

The N-hydroxy-alpha-amino acid amides according to the invention can be converted into the corresponding acids, esters and other derivatives.

The hydrolysis of the amides discussed here to the corresponding N-hydroxy-alpha-amino acids can, with particular advantage, be effected enzymatically, with the aid of an amido hydrolase, for example as described in NL-A-84.03093. When this enzymatic hydrolysis is completed, the remaining enzymes are removed, for example by centrifugation, after which sufficiently pure N-hydroxy-alpha-amino acid can be recovered, for example by evaporating the solution. As compared with this, the hydrolysis of the amides discussed here with the aid of acids constitutes a considerable burden on the environment. Another important advantage of enzymatic hydrolysis is that it can be effected at a pH between 6 and 10. In an acid medium N-hydroxy-alpha-amino acids are only moderately stable, much less stable than the corresponding alpha-amino acids at the same pH. In an acid medium N-hydroxy-alpha-amino acids are easily decarboxylized, particularly when heating is applied, as is necessary in acid hydrolysis.

The N-hydroxy-alpha-amino acids according to the invention can be converted into esters or other derivatives in a known manner.

The N-hydroxy-alpha-amino acids or derivatives thereof according to the present invention can also be used for the preparation of N-hydroxypeptides, a group of compounds that is also discussed in the article by Ottenheym and Herscheid (loc. cit.)

The invention is further elucidated with the following examples.

These examples describe ways in which to prepare stereoisomers that are not or hardly contaminated by one or more other stereoisomers. Of course, the invention is not at all limited to these examples and comprises both other stereoisomers and mixtures of stereoisomers. The invention is not limited by the examples in any other way either.

EXAMPLE I a) 12.5 g (0.11 mol) of D-valine amide was dissolved to a 10 wt % solution in water with stirring and gentle heating to 40° C. The pH was set to at least 11 by adding 1N KOH. Then 16.5 g (0.12 mol) of anisaldehyde (4-methoxybenzaldehyde) was added dropwise, with stirring, over a period of about 15 minutes. The mixture was allowed to cool to room temperature and the stirring was continued for about 2 hours. Then the precipitated Schiff base of D-valine amide and anisaldehyde was removed by filtration, washed with water to remove anisaldehyde remains and dried. The yield was almost quantitative (98%).

b) 23.4 g (0.1 mol) of the Schiff base of D-valine and anisaldehyde prepared according to Ia) was dissolved, with stirring, in 130 ml of dry dichloromethane. The solution was cooled to 5° C. or lower in an ice bath. Then 20.6 g (0.12 mol) of meta-chloroperbenzoic acid was added, with stirring, to the solution cooled to 5° C. or lower. The stirring was continued and the temperature was allowed to rise to room temperature, after which the stirring was continued for 4 more hours. After about 0.5 hour's stirring at room temperature the mixture became turbid as a result of the crystallization of meta-chlorobenzoic acid. After the reaction, in which all the meta-chlorobenzoic acid formed crystallized, the reaction mixture was filtered and the filtered solution was evaporated until dry.

c) The evaporation residue obtained according to Ib) was dissolved in 150 ml of methanol. With stirring, 7.0 g (0.10 mol) of hydroxylamine hydrochloride was slowly added to this solution, a small portion at a time, after which the stirring was continued for 3 more hours at room temperature. The reaction mixture thus obtained was then added dropwise to 1 l of diethyl ether. A white precipitate of D-N-hydroxyvaline amide.HCl was formed, which was removed by filtration and dried. Yield: 12.8 g (76%).

$[alpha]^{20}_D = -73°$. (c=1, H$_2$O).

d) 8.4 g of the D-N-hydroxyvaline amide.HCl was dissolved in 100 ml of methanol. The solution was transferred to a Parr apparatus along with a 5% Pd on carbon catalyst (5 mol % Pd with respect to the hydroxyvaline amide) and reduced with hydrogen. After hydrogenation the Pd/catalyst was removed by filtration and the solution in methanol was evaporated. The specific rotation of the hydrogenated product appeared to be the same as that of D-valine amide.HCl, namely $-28.3°$. This shows that the preparation of D-N-hydroxyvaline amide.HCl from D-valine amide.HCl according to b) takes place without racemization.

EXAMPLE II a) The Schiff base of D-phenyglycine amide and anisaldehyde was prepared in the same manner as in example I.

b) 26.8 g (0.1 mol) of the Schiff base of D-phenylglycine amide and anisaldehyde was dissolved in 115 ml of dry dichloromethane. The solution was cooled to 0° C. in an ice bath and then 24.3 g (0.12 mol) of meta-chlorobenzoic acid was added, with stirring. With stirring, the temperature was allowed to rise to room temperature, after which the stirring was continued for 4 more hours. After approximately ¼ hour's stirring at room temperature the mixture became turbid as a result of the crystallization of m-chlorobenzoic acid. After the reaction, in which all the m-chlorobenzoic acid formed had crystallized, the reaction mixture was filtered, after which the filtered solution was evaporated until dry.

c) The evaporation residue obtained according to IIb) was dissolved in 150 ml of methanol. With stirring, 7.0 g (0.10 mol) of hydroxylamine hydrochloride was slowly added to this solution, a small portion at a time, after which the mixture was stirred for 5 more hours at room temperature. With stirring, the reaction mixture thus obtained was then added dropwise to 2 l of diethylether. A white precipitate of D-N-hydroxyphenylglycine amide.HCl was formed, which was removed by filtration and dried. Yield: 17.6 g (85%).

$[alpha]^{20}_D = -107.5°$ (c=1, MeOH).

d) 6.3 g of D-N-hydroxyphenylglycine amide.HCl was dissolved in 10 ml of water, after which 2.12 g of sodium carbonate, free from water, was added to the solution, with stirring. A precipitate was formed, which was removed by filtration, washed twice with 5 ml of water and then dried.

Yield: 4.5 g of D-N-hydroxyphenylglycine amide.H$_2$O.

$[alpha]^{20}_D = -57.6°$ (c=1, MeOH)

NMR (DMSO): delta, dpm: 4.32 (H alpha), 6.10 (N-H), 7.54 (OH), 7.14/7.42 (CONH$_2$), 7.2–7.4 (phenyl), J (H alpha, NH)=8 Hz, J (NH, OH)=2 Hz.

e) The preparation processes described in sections a), b) and c) of this example were repeated using L-phenylglycine amide instead of D-phenylglycine amide. This resulted in the same yield of L-N-hydroxyphenylglycine amide.HCl with $[alpha]^{20}_D = +107.5°$ (c=1, MeOH).

EXAMPLE III

In the same way as in example II the Schiff bases of D-phenylalanine amide and anisaldehyde and of L-phenylalanine amide and anisaldehyde were prepared in two experiments. Of each of these bases a solution was prepared of 21.0 g (0.074 mol) in 140 ml of dichloromethane. The solutions were cooled to 0° C. in an ice bath, after which 16.1 g (0.09 mol) of meta-chloroperbenzoic acid was added to each solution, with stirring, after which the cooling was stopped to allow the temperature to rise to room temperature. The solutions, in which after 10 minutes already a precipitate started to form, were stirred for 4.5 hours, after which the precipitate was removed by filtration. The solutions were dried by evaporation and the evaporation residues were each dissolved in 100 ml of methanol, after which 6.3 g of hydroxylamine hydrochloride was added to each solution. After 7 hours' stirring at room temperature, 2 l of diethyl ether was slowly added to each solution. The resulting precipitates were removed by filtration and dried. Yields: 13.4 g (86%) of D-N-hydroxyphenylalanine amide.HCl and 13.0 g (83%) of L-N-hydroxyphenylalanine amide.HCl.

By dissolving 6.7 g of these compounds in 10 ml of water and adding 2.12 g of sodium carbonate, free from water, 5.4 g of D-N-hydroxyphenylalanine amide.H$_2$O and the corresponding L-compound were prepared, which had specific rotations of $-4.1°$ (D) and $+4.3°$ (L), respectively. (c=1, MeOH).

NMR (DMSO): delta, dpm: 2.62 (H beta), 2.77 (H beta), 3.45 (H alpha), 5.59 (N—H), 7.41 (OH), 7.01/7.15 (CONH$_2$), 7.1–7.3 (phenyl), J (H beta 1, H beta 2)=14 Hz, J (H beta 1, H alpha)=8 Hz, J (H beta 2, H alpha)=5.5 Hz, J (H alpha, NH)=8.5 Hz, J (NH, OH)=3 Hz.

EXAMPLES IV–VIII

In the same way as described in the previous examples, L-N-hydroxyleucine amide.HCl was prepared from L-leucine amide (example IV) with a yield of 65% and the corresponding N-hydroxy compounds were prepared from racemic mixtures of phenylglycine amide (example V), phenylalanine amide (example VI) and valine amide (example VII).

In the same manner D,L-alpha-methyl-alpha-N-hydroxy-valine amide.HCl was prepared from the Schiff base of anisaldehyde and alpha-methylvaline amide (racemic mixture) (example VIII).

We claim:

1. The D- or L- stereo-isomer of a compound with the formula

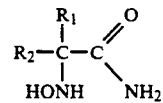

in substantially optically pure form, in which $R_1$ represents H, acyclic or cyclic alkyl or carbocyclic aryl and $R_2$ represents H, acyclic or cyclic alkyl or carbocyclic aryl, with the following proviso regarding combinations of $R_1$ and $R_2$: $R_1$ and $R_2$ are not, respectively, H and H; nor $CH_3$ and $CH_3$; nor H and $CH_3$; nor $CH_3$ and H.

2. A compound according to claim 1, in which one of the symbols $R_1$ and $R_2$ represents H.

3. L-N-hydroxy-phenylglycine amide, in substantially optically pure form.

4. D-N-hydroxy-phenylglycine amide, in substantially optically pure form.

* * * * *